United States Patent
Bissmann et al.

(10) Patent No.: US 9,545,341 B2
(45) Date of Patent: Jan. 17, 2017

(54) METHOD FOR OPTIMIZED PREDICTION OF THE POSTOPERATIVE ANATOMICAL POSITION OF AN INTRAOCULAR LENS IMPLANTED IN A PSEUDOPAKIC EYE

(75) Inventors: Wilfried Bissmann, Jena (DE); Tobias Bühren, Magdala (DE); Michael Trost, Stadtroda (DE)

(73) Assignee: Carl Zeiss Meditec AG, Jena (DE)

( * ) Notice: Subject to any disclaimer, the term of this patent is extended or adjusted under 35 U.S.C. 154(b) by 336 days.

(21) Appl. No.: 14/130,120

(22) PCT Filed: Jul. 5, 2012

(86) PCT No.: PCT/EP2012/063190
§ 371 (c)(1),
(2), (4) Date: Dec. 30, 2013

(87) PCT Pub. No.: WO2013/004800
PCT Pub. Date: Jan. 10, 2013

(65) Prior Publication Data
US 2014/0125955 A1 May 8, 2014

(30) Foreign Application Priority Data
Jul. 6, 2011 (DE) .................. 10 2011 106 714

(51) Int. Cl.
*A61B 3/00* (2006.01)
*A61F 9/013* (2006.01)
(Continued)

(52) U.S. Cl.
CPC .............. *A61F 9/013* (2013.01); *A61B 3/10* (2013.01); *A61B 3/1005* (2013.01); *A61F 2/16* (2013.01);
(Continued)

(58) Field of Classification Search
CPC ..... A61B 3/0025; A61B 3/1005; A61B 3/107; A61B 3/14; A61B 3/152; A61F 2240/002; A61F 2/1613
(Continued)

(56) References Cited

U.S. PATENT DOCUMENTS 5,282,852 A   2/1994   Capetan et al.
5,968,095 A  10/1999   Norrby
(Continued)

FOREIGN PATENT DOCUMENTS

WO   WO 2006/053216 A2   5/2006
WO   WO 2010/065139 A2   4/2010
WO   WO 2011/008609 A1   1/2011

OTHER PUBLICATIONS

Paul Rolf Preussner et al., "Predicting postoperative intraocular lens position and refraction", Journal Cataract and Refractive Surgery, Fairfax, VA, US, vol. 30, No. 10, Oct. 1, 2004, pp. 2077-2083.
(Continued)

*Primary Examiner* — Mahidere Sahle
(74) *Attorney, Agent, or Firm* — Patterson Thuente Pedersen, P.A.

(57) ABSTRACT

Postoperative lens position is predicted on the basis of known measured values, such as the corneal thickness, the depth of the anterior chamber, the eye length, and the distances of the capsular bag equator and/or of the lens haptic from the anterior surface of the lens. In addition, the calculation also takes into account the attitude of the intraocular lens, for which purpose additional parameters of the pseudophakic eye are used that have not previously been taken into consideration. The proposed method is suitable for a more exact prediction of the strength and nature of an intraocular lens to be implanted in a pseudophakic eye in the context of cataract surgery or of a refractive intervention. The method is based on the use of suitable calculation methods, e.g. geometric optical formulae, or of ray tracing.

24 Claims, 2 Drawing Sheets

(51) Int. Cl.
*A61B 3/10* (2006.01)
*A61F 2/16* (2006.01)
(52) U.S. Cl.
CPC .. *A61F 2002/1681* (2013.01); *A61F 2240/002* (2013.01)
(58) Field of Classification Search
USPC .................................................. 351/200–247
See application file for complete search history.

(56) References Cited

U.S. PATENT DOCUMENTS

| | | | | |
|---|---|---|---|---|
| 7,878,655 | B2* | 2/2011 | Salvati | A61B 3/0025 351/221 |
| 2007/0260157 | A1 | 11/2007 | Norrby et al. | |
| 2009/0164007 | A1 | 6/2009 | Van Heugten | |
| 2009/0251664 | A1 | 10/2009 | Norrby et al. | |

OTHER PUBLICATIONS

Preussner, P.-R. et al: "Intraocular lens calculation accuracy limits in normal eyes," J Cataract Refreact Surg—vol. 34, May 2008; 802-808.
Notification of Transmittal of Translation of the International Preliminary Report on Patentability (Chapter I or Chapter II) PCT/IB/338, PCT International Preliminary Report on Patentability Form PCT/IB/373, PCT Written Opinion of the International Searching Authority PCT/ISA/237 for PCT/EP2012/063190 (9 total pages).

* cited by examiner

Sample function for ALP offset as a function of KRSR

Y axis: ALP offset
X axis: Ratio of capsulorhexis diameter to capsular bag diameter Sample function for ALP offset as a function of KLHDR Y axis: ALP offset
X axis: Ratio of capsular bag diameter to lens haptic diameter

METHOD FOR OPTIMIZED PREDICTION OF THE POSTOPERATIVE ANATOMICAL POSITION OF AN INTRAOCULAR LENS IMPLANTED IN A PSEUDOPAKIC EYE

RELATED APPLICATIONS

The present application is a National Phase entry of PCT Application No. PCT/EP2012/063190, filed Jul. 5, 2012, which claims priority from DE Application No. 10 2011 106 714.4, filed Jul. 6, 2011, which applications are hereby incorporated by reference herein in their entirety.

FIELD OF THE INVENTION

The present invention relates to a method for the preoperative selection of an intraocular lens to be implanted in an eye. In doing so, the results of the refractive intervention on the eye are to be optimized by application of a prediction of the postoperative, anatomical position of the implanted intraocular lens.

BACKGROUND

According to known prior art, intraocular lens (IOLs) are selected and adjusted based on the measured and/or estimated measurements, wherein only individual parameters in the form of individual measurement values or as a mean value over specified patient groups are taken into consideration.

In this regard, the selection and adjustment of the optimal IOL takes place solely according their features, such as type, refractive power, asphericity, and multifocality. Taking into account possible dependencies on specific accompanying circumstances of the treatment, such as characteristics of the patients, diagnoses, surgical procedures, and similar, occurs just as infrequently as the use of statistical distribution for the parameters.

Selecting the suitable intraocular lens for a patient is the responsibility of the cataract surgeon. In this regard, the surgeon must take into consideration many factors. First, depending on the individual biometric parameters of the eye, the suitable calculation method of the IOL refractive power should be selected. To do so, generally for extraordinarily long, normal, or extraordinarily short eyes, various more or less suited formulas are used for calculation purposes. In the simplest situation, their input parameters are based on keratometry and axis lengths of the eye, wherein the formulas, due to their simplified model assumptions, also contain an empirically determined correction factor, such as the so-called A constant, for example.

The currently most widespread calculation methods are the so-called IOL formulas, e.g., according to Haigis, Holladay, Hoffer, Olsen, Shammas, or SRK. Accordingly, refraction D (output/evaluation parameter) of the patient is calculated after inserting the IOL by $$D = D_{IOL} - f(K, AL, VKT, A) \quad (1)$$

wherein f( ) is a conventionally known IOL formula
$D_{IOL}$ is the refractive power of the IOL,
K is the measured keratometry value,
AL is the measured axis length of the eye,
VKT is the measured depth of the anterior chamber and
A is an IOL-type-dependent constant input value.

The various calculation methods (biometry formulas) generally use various IOL-type-dependent constants (i.e., IOL constants). An A constant is used in the SRK formula for example.

For selecting the IOL, the physician sets a target refraction (D=Dtarget). For optimization purposes, the physician calculates the refraction (1) according to various IOLs by varying DIOL and A. In many cases, the physician uses IOLs of the same type, so that no variation in A results, and the optimization boils down to a formula calculation according to $D_{IOL}$=Dtarget+f(K, AL, VKT, A). If emmetropia is the objective, this results in the traditional formula calculation of the IOL according to $D_{IOL}$=f(K, AL, VKT, A).

The constant A in the formulas is determined empirically via a patient group to adapt the formula values to the actually resulting optimal refraction values. However, this adaptation only ensures that the mean value of the refraction values agrees with the formula over the test group.

To minimize systematic errors, currently other approaches are being selected according to prior art.

For example, a series of physicians uses a different A constant for each ethnic group among their patients. In this way, errors can be systematically reduced and, to the extent the statistical scatter in the respective group is lower, so can the statistical errors.

Depending on specified starting conditions, such as patients with long axis lengths or with prior refractive corneal surgery, other physicians use various biometry formulas that are better adapted to the respective requirements, or that presuppose the measurement of additional parameters, such as anterior chamber depths or lens thickness. Here, too, systematic errors in particular are decreased, wherein however, the statistical errors can increase partially due to the additionally measured parameters.

Presupposing or predicting the postoperative position i.e., the "effective" orientation of the implanted intraocular lens in the eye, plays a major role. Various formulas pertain to determining the postoperative ELP of various assumptions, based on diverse biometric parameters of the eye. In the simplest case, these are: keratometry and axis length of the eye. Fourth-generation formulas, as they are called, use up to six parameters for predicting the ELP, such as: axis length, anterior chamber depth, keratometry, lens thickness, limbus diameter, and age of the patient. Due to the simplified model assumptions of the eye, as well as the "empirical" nature of the many formulas, i.e., optimization of the formula results via constants, "virtual" values result for the calculated ELP, so that the ELP required for an optimized result does not generally correspond to the actual anatomical lens position in the eye. The reason for this is that due to the postoperative refraction results and the resulting average error correction (e.g., through the A constant), only the predicted ELP can change because all other parameters were measured. Optimization via constants does not take into account that other preoperatively measured parameters could have changed postoperatively in addition to the expected refraction result.

Another method to predict the ELP is based on the principle of determining the capsular bag equator and is described in U.S. Pat. No. 5,968,095 A. In doing so, the distance of the lens haptic to the anterior surface of individual IOL designs is taken into account. The orientation of the capsular bag equator can thus be determined in various ways. With this method, one can theoretically achieve a prediction of the ELP that is independent of the individual IOL design.

In contrast to the postoperative effective lens position (ELP), which due to the simplified model assumption of the eye as well as empirical formulas does not generally correspond to the actual anatomical lens position, the anatomical postoperative lens position defines the actual, i.e., real, postoperative position of the intraocular lens to be implanted.

The term "haptic" refers to the support structure existing for fixing the intraocular lens in the eye. The haptics are arranged peripherally to the actual optic lens and may be constructed in various shapes, such as brackets, plates, or straps.

In the known IOL design-dependent or independent methods according to prior art for predicting or determining the postoperative ELP, a disadvantageous effect is that none of the known methods can do without empirical correction factors. One reason for this are individual postoperative healing processes that usually last over a period of several weeks, which is not taken into account in the methods known to date. Another reason may be seen in that despite diverse methods, only an insufficient number of parameters relevant for determining the ELP is taken into account in the prediction.

Another problem lies in the optimization method of the formula approaches. Improving the postoperative refraction results by application of the constant procedure takes into consideration all errors occurring in cataract surgery. These are errors in the measurement procedures, errors in the IOL calculation, and unexpected events during the implantation and healing processes. However, optimizing the results solely by use of postoperative refraction excludes individual error sources from being taken into account.

SUMMARY OF THE INVENTION

The invention is to eliminate the disadvantages of the solutions known from prior art and to optimize the prediction of the postoperative lens position of an intraocular lens to be implanted in a pseudophakic eye.

This object is achieved with the method according to the invention for optimizing the prediction regarding the postoperative lens position of an intraocular lens to be implanted in a pseudophakic eye, for which said lens calculations are performed by known measurements, such as corneal thickness, anterior chamber depth, eye length, as well as the distance of the capsular bag equator and lens haptics to the anterior surface of the lens, in that besides the anatomical, postoperative position of the intraocular lens to be implanted, their orientation is also included in the calculation, for which additional parameters not taken into account before of the pseudophakic eye, such as the diameter of the capsular bag equator and capsulorhexis, the preoperative decentration and tilting of the eye lens, the center of the pupil region, as well as the haptic diameter and the haptic-type of the intraocular lens used are taken into account.

The term "capsulorhexis" refers to the disk-shaped opening of the anterior surface of the capsular bag and represents an elegant method within the scope of a cataract treatment, in which the capsular bag is perforated and opened by a tearing maneuver.

The proposed method according to the invention is suited for a more exact prediction of the strength and type of an intraocular lens to be implanted in a pseudophakic eye within the scope of a surgical cataract or refractive intervention. In doing so, the method is based on the use of suitable calculation methods, e.g., geometric-optic formulas or ray tracing, in which, besides known measurement values, pseudophakic eye parameters not taken into account to date are also used.

BRIEF DESCRIPTION OF THE DRAWINGS

The invention will be described hereafter in greater detailed using embodiments.

DETAILED DESCRIPTION

In the method according to the invention for optimally predicting the postoperative lens position ($LP_{an\text{-}post}$) of an intraocular lens (L) to be implanted in a pseudophakic eye by application of known measurement values, such as the corneal thickness (HHD), the anterior chamber depth (VKT), the eye length (AL) as well as the distances of the capsular bag equator (KSA) and the lens haptics (LH) of the anterior surface of the lens (LV), besides the anatomical, postoperative position ($LP_{an\text{-}post}$) of the intraocular lens (L) to be implanted, their orientation ($LL_{an\text{-}post}$) is also included in the calculation, for which purpose additional, not yet considered parameters of the pseudophakic eye are used. As additional parameters of the pseudophakic eye, the diameter of the capsular bag and capsulorhexis, the preoperative decentration, and tilting of the eye lens, the center of the pupil region (PBM), as well as the haptic diameter (LHD) and the haptic-type (LHT) of the used intraocular lens (L) are taken into account.

Figure 1:
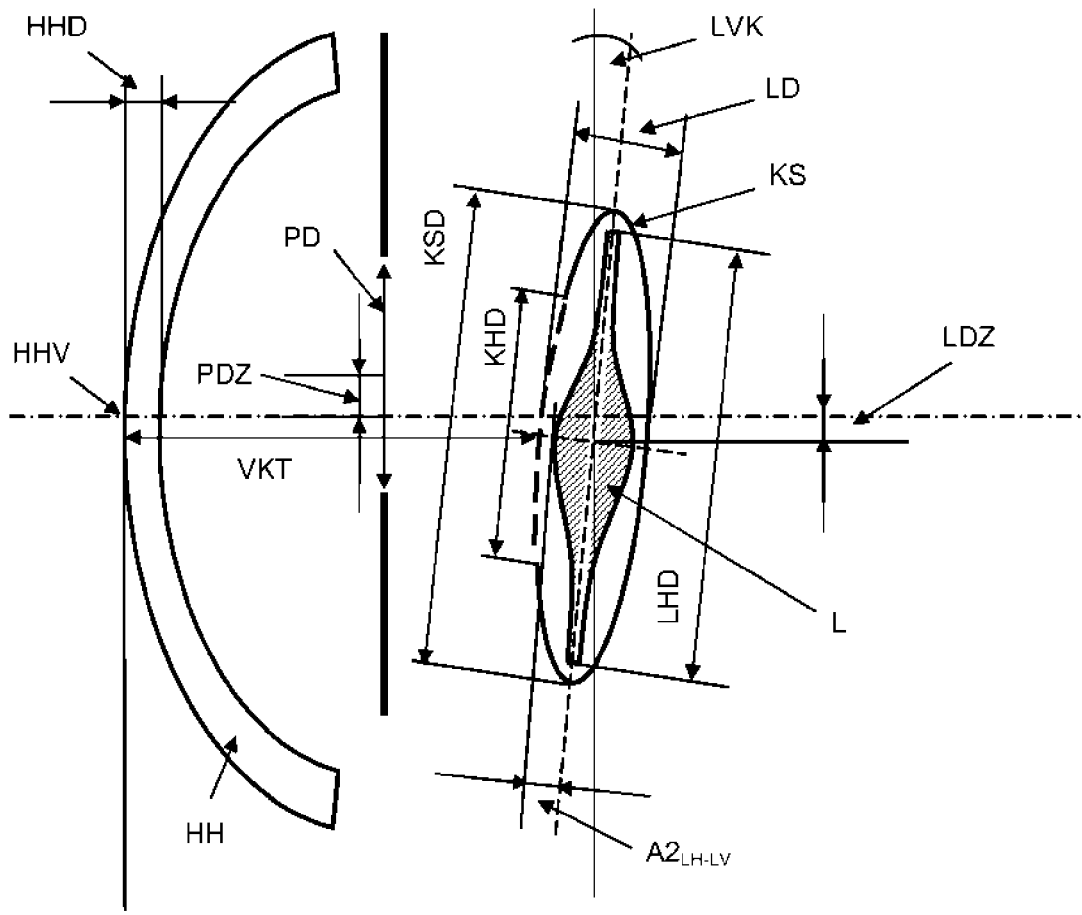
FIG. 1 depicts a schematic diagram of the anterior eye segments with the corresponding parameters.

To this end, FIG. 1 depicts a schematic diagram of the anterior eye segments with their components and the corresponding parameters. An overview of the abbreviations used is provided in the list of reference signs.

In a first embodiment of the method according to the invention, the postoperative, anatomical lens position $LP_{an\text{-}post}$ results from the following formula:

$$LP_{an\text{-}post} = VKT - HHD + A1_{KSA\text{-}LV} \quad (2)$$

in which
VKT characterizes the anterior chamber
HHD characterizes the corneal thickness and
$A1_{KSA\text{-}LV}$ characterizes the distance between the capsular bag equator and the anterior surface of the lens and distance $A1_{KSA\text{-}LV}$ stems from the following formula:

$$A1_{KSA\text{-}LV} = (LD/3 - A2_{LH\text{-}LV}) + f(V1_{KSD\text{-}KHD}) + f(V2_{KSD\text{-}LHD}) + f(LHT) \quad (3)$$

in which
LD characterizes the lens thickness,
$A2_{LH\text{-}LV}$ characterizes the distance between lens haptics and the anterior surface of the lens
$f(V1_{KSD\text{-}KHD})$ characterizes a function of the ratio of the capsule sack diameter to the capsulorhexis,
$f(V2_{KSD\text{-}KHD})$ characterizes a function of the ratio of the capsular bag diameter to the lens haptic and
$f(LHT)$ characterizes a function of the lens haptic-type Accordingly, the ratios $V1_{KSD\text{-}KHD}$ and $V2_{KSD\text{-}LHD}$, as well as the influence of the lens haptic-type LHT used are determined empirically in studies and quantified as a function.

Accordingly, it is possible that the functions $f(V1_{KSD\text{-}KHD})$ and $f(V2_{KSD\text{-}LHD})$ are determined for individual or also for a number of different lens designs.

The ratio of the capsular bag to capsulorhexis diameters results hereby as function $f(V1_{KSD\text{-}KHD})$ from the following formula:

$$f(V_{KSD\text{-}KHD}) = KHD/KSD \cdot KSD_{norm}/KHD_{norm} \quad (4)$$

in which
- KHD characterizes the diameter of the capsulorhexis,
- KSD characterizes the diameter of the capsular bag,
- $KSD_{norm}$ characterizes the individual mean diameter of the capsular bag and
- $KHD_{norm}$ characterizes the capsulorhexis diameter empirically determined as a function of various parameters wherein for example the pathology, ethnic origin, sex, and age can be taken into account as an empirical scaling function.

Figure 2:
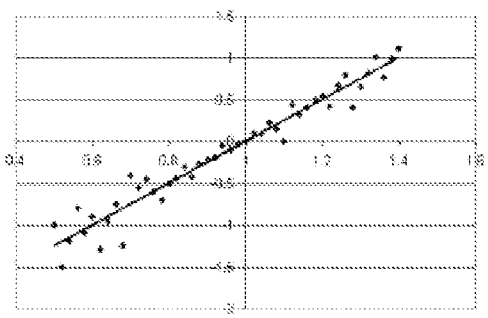
FIG. 2 depicts a sample representation of the dependency of the anatomical lens position on the ratio of the capsular bag diameter to capsulorhexis.

To this end, FIG. 2 depicts a sample representation of the dependency of the anatomical lens position through the ratio of the capsular bag diameter to the capsulorhexis diameter. This dependency is to be determined empirically in studies and quantified as a function, whereby the resulting function can change according to the selected scaling function, e.g., the pathology, ethnic origin, sex, age or similar. Accordingly, it is also possible that no function can be quantified.

The representation for example purposes shows distance $A1_{KSA\text{-}LV}$ resulting as a function of the ratio of the capsular bag diameter to the capsulorhexis diameter, said distance included as a correction value via formula (3) in formula (2), from which an optimized value thus results for the postoperative, anatomical lens position $LP_{an\text{-}post}$.

Correspondingly, the ratio of the capsular bag diameter to the lens haptic diameter as a function $f(V2_{KSD\text{-}LHD})$ results from the following formula:

$$f(V2_{KSD\text{-}LHD}) = LHD/KSD \cdot KSD_{norm}/LHD \quad (5)$$

in which:
- LHD characterizes the specific diameter of the lens haptic,
- KSD characterizes the diameter of the capsular bag and
- $KSD_{norm}$ characterizes an individual mean diameter of the capsular bag wherein in turn for example the pathology, ethnic origin, sex, and age can be taken into account as empirical scaling functions.

Figure 3:
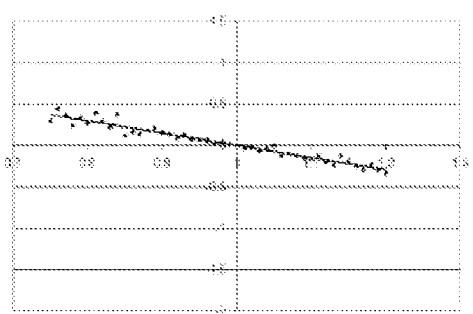
FIG. 3 depicts a sample representation of the dependency of the anatomical lens position on the ratio of the capsular bag diameter to the haptic.

To this end, FIG. 3 depicts a sample representation of the dependency of the anatomic lens position on the ratio of the capsular bag diameter to the haptic diameter. This dependency is also to be determined empirically in studies and quantified as a function, wherein the resulting function can in turn change depending on the selected scaling function, e.g., the pathology, ethnic origin, sex, age or similar. Here too, it is possible that no function can be quantified.

The representation for example purposes shows distance $A1_{KSA\text{-}LV}$ resulting as a function of the ratio of the capsular bag diameter to the haptic diameter, said distance included as a correction value via formula (3) in formula (2), from which an optimized value thus results for the postoperative, anatomical lens position $LP_{an\text{-}post}$.

If in contrast to the representations depicted in FIGS. 2 and 3, no dependencies can be discerned in the ratios of the capsular bag diameter to the capsulorhexis diameter $V1_{KSD\text{-}KHD}$ or capsular bag diameter to lens haptic diameter $V2_{KSD\text{-}LHD}$, then $f(V1_{KSD\text{-}KHD})$ and $f(V2_{KSD\text{-}LHD})$ each take on the value of zero.

In a second embodiment of the method according to the invention, the postoperative, anatomic lens orientation $(LL_{an\text{-}post})$ can be described by the following three parameters:
- LDZ—horizontal and vertical decentration of the lens,
- LVK—horizontal and vertical tilting of the lens and
- PBM—center of the pupil region that can be used in the calculation.

Accordingly, the horizontal and vertical decentration LDZ of the lens results from the following formula:

$$LDZ = LDZ_{eye} \times f(LDZ_{eye}) \quad (6)$$

in which
- $LDZ_{eye}$ characterizes the horizontal and vertical decentration of the actual eye lens and
- $f(LDZ_{eye})$ characterizes an empirical function of the decentration of the actual eye lens wherein for example the pathology, the ethnic origin, sex, and age can be taken into account as empirical scaling functions.

Correspondingly, the horizontal and vertical tilting LVK of the lens results from the following formula:

$$LVK = LVK_{eye} \times f(LVK_{eye}) \quad (7)$$

in which
- $LVK_{eye}$ characterizes the horizontal and vertical tilting of the actual eye lens and
- $f(LVK_{eye})$ characterizes an empirical function of the tilting of the decentration of the actual eye lens wherein in turn the pathology, ethnic origin, sex, and age for example can be taken into account as empirical scaling functions.

The center of pupil region PBM that can be used for the calculation stems in contrast from the following formula:

$$PBM = HHV - PDZ - LDZ \quad (8)$$

in which
- HHV characterizes the corneal vertex,
- PDZ characterizes the horizontal and vertical decentration of the pupil and
- LDZ characterizes the horizontal and vertical decentration of the lens Accordingly, it is here also possible that the empirically determined scaling functions are determined for individual or also a number of different lens designs.

According to a third advantageous embodiment of the method according to the invention, it is hereby possible that the postoperative, anatomic lens orientation $LL_{an\text{-}post}$ or the center of the pupil region PBM usable for the calculation can be determined on various pupil apertures, such as photopic, scotopic, or mesopic vision.

According to another example embodiment of the method according to the invention for optimally predicting the anatomical, postoperative position $LP_{an\text{-}post}$ of an intraocular lens to be implanted in a pseudophakic eye, calculation methods, such as geometric-optical formulas or ray tracing, can be used to calculate the intraocular lens L to be implanted.

The method according to the invention is based on the assumption that the postoperative positioning or displacement of the (IOL) lens is determined within the scope of the healing process by the "fit-ability of the preoperative capsular bag to the size and shape of the (IOL) lens haptic as well as the capsulorhexis.

By the possible inclusion of additional parameters that describe the insertion of the lens in the capsular bag, a more exact prediction of the anatomical, postoperative lens position is made possible.

The parameters listed in FIG. 1 of the reference sign list can be directly determined only to a partial degree using today's conventional technology. For example, the capsular bag diameter and the distance of the capsular bag equator to the cornea cannot be determined by optical means. For that reason, a component of the solution is the use of an image of the eye section that comprises at least the anterior corneal surface all the way to the rear surface of the capsular bag. Such an image can be obtained by means of Scheimpflug photography or OCT technology. From the parts, made visible in this image of the posterior and anterior lens surface and suitable software algorithms, the image can be completed to the capsular bag equator so that the distance of the cornea to the capsular bag equator, as well as the capsular bag diameter can be determined.

In addition, it shall be assumed that the natural human lens is generally tilted and decentered due to physiological reasons. For that reason, an additional assumption underlying the solution is that the implanted intraocular lens is also positioned in the eye in a tilted and decentered manner and that the pre- and postoperative decentering and tilting correlate.

With the solution according to the invention, a method for predicting the anatomical, postoperative position of an intraocular lens to be implanted in a pseudophakic eye is provided, with which, in addition to the lens position, the lens orientation of the intraocular lens to be implanted can be predicted in a more optimized and thus more precise manner.

Predicting or optimizing the prediction of the anatomical, postoperative lens position is achieved by application of parameters not taken into account to date and is thus independent of the postoperative refraction result. Erroneous postoperative refraction results, which are not caused by an erroneous anatomical lens position, are not taken into account in predicting the anatomical lens position.

For the prediction, not only are the capsular bag equator and the distance of the lens haptic to the anterior surface of the lens take into account in the prediction, but also the capsular bag diameter, the capsulorhexis diameter, the corneal thickness, the preoperative lens decentration, and lens tilting, as well as the haptic diameter and haptic type of the (IOL) lens.

By application of the method according to the invention, the exact prediction of the anatomical, postoperative position of the intraocular lens to be implanted is possible for each individual eye.

REFERENCE LIST

L (IOL) lens
$LP_{an-post}$ anatomical, postoperative position of the (IOL) lens
$LL_{an-post}$ anatomical, postoperative orientation of the (IOL) lens
HHD corneal thickness
HHV corneal vertex
VKT anterior chamber depth
KS capsular bag
KSA capsular bag equator
KSD capsular bag diameter
$KSD_{norm}$ mean diameter of capsular bag
KH capsulorhexis
KHD capsulorhexis diameter
$KHD_{norm}$ empirically determined diameter of capsulorhexis
LD lens thickness (of the IOL)
LH lens haptic (of the IOL)
LHD lens haptic diameter
LHT lens haptic-type
LV anterior surface of lens (IOL)
$A1_{KSA-LV}$ distance A1 between the capsular bag equator and the anterior surface of the lens
$A2_{LH-LV}$ distance A2 between the lens haptic and the anterior surface of the lens
$V1_{KSA-KHD}$ ratio of the capsular bag and capsulorhexis diameters
$V2_{KSD-LHD}$ ratio of the capsular bag to the lens haptic
LDZ horizontal and vertical decentration of the (IOL) lens
$LDZ_{eye}$ horizontal and vertical decentration of the actual eye lens
LVK horizontal and vertical tilting of the (IOL) lens
$LVK_{eye}$ horizontal and vertical tilting of the actual eye lens
PD pupil diameter
PDZ horizontal and vertical decentration of the pupil
PBM center of the pupil region that can be used for the calculation

The invention claimed is:

1. A method for optimized prediction of postoperative lens position ($LP_{post}$) of an intraocular lens to be implanted in a pseudophakic eye, comprising:
   using known measurement values, including corneal thickness (HHD), anterior chamber depth (VKT), eye length (AL) as well as the distance of the capsular bag equator (KSA) or lens haptic (LH) to the anterior surface of the lens (LV) for calculation; and
   including in the calculation an anatomical, postoperative position ($LP_{an-post}$) of the intraocular lens (L) to be implanted and an orientation ($LL_{an-post}$) of the intraocular lens and additional parameters not yet taken into account of the pseudophakic eye.

2. The method according to claim 1, further comprising taking into account at least one factor selected from a group consisting of a diameter of the capsular bag and a diameter of a capsulorhexis, a preoperative decentration and a tilting of the eye lens, a center of the pupil range (PBM), a haptic diameter (LHD) and a haptic type (LHT) of the intraocular lens (L) used.

3. The method according to claim 1, further comprising determining a postoperative, anatomical lens position ($LP_{an-post}$) from formula (2):

$$LP_{an-post} = VKT - HHD + A1_{KSA-LV} \quad (2)$$

in which
   VKT represents the anterior chamber depth
   HHD represents the corneal thickness and
   $A1_{KSA-LV}$ represents the distance between the capsular bag equator and the anterior surface of the lens and determining distance $A1_{KSA-LV}$ from formula (3):

$$A1_{KSA-LV} = (LD/3 - A2_{LH-LV}) + f(V1_{KSD-KHD}) + f(V2_{KSD-LHD}) + f(LHT) \quad (3)$$

in which LD represents the lens thickness,
   $A2_{LH-LV}$ represents the distance between the lens haptic and the anterior surface of the lens,
   $f(V1_{KSD-KHD})$ represents a function of the ratio of the capsular bag to capsulorhexis diameters
   $f(V2_{KSD-KHD})$ represents a function of the ration of the capsular bag to the lens haptic diameter s and
   f(LHT) represents a function of lens haptic type.

4. The method according to claim 2 further comprising determining a postoperative, anatomical lens position ($LP_{an-post}$) from formula (2):

$$LP_{an-post} = VKT - HHD + A1_{KSA-LV} \quad (2)$$

in which
- VKT represents the anterior chamber depth
- HHD represents the corneal thickness and
- $A1_{KSA-LV}$ represents the distance between the capsular bag equator and the anterior surface of the lens.

5. The method according to claim 3, further comprising empirically determining the ratios $V1_{KSD-KHD}$ and $V2_{KSD-LHD}$, and the influence of the lens haptics-type LHT in studies and quantifying the ratios $V1_{KSD-KHD}$ and $V2_{KSD-LHD}$, and an influence of the lens haptics-type LHT as functions.

6. The method according to claim 4, further comprising empirically determining the ratios $V1_{KSD-KHD}$ and $V2_{KSD-LHD}$, and the influence of the lens haptics-type LHT in studies and quantifying the ratios $V1_{KSD-KHD}$ and $V2_{KSD-LHD}$, and an influence of the lens haptics-type LHT as functions.

7. The method according to claim 5, further comprising determining the functions $f(V1_{KSD-KHD})$ and $f(V2_{KSD-LHD})$ for individual lens designs or for a number of different lens designs.

8. The method according to claim 3, wherein $f(V1_{KSD-KHD})$ results as a function from the ratio of the capsular bag to capsulorhexis diameters from formula (4):

$$f(V1_{KSD-KHD})=KHD/KSD \cdot KSD_{norm}/KHD_{norm} \quad (4)$$

in which
- KHD represents the diameter of the capsulorhexis
- KSD represents the diameter of the capsular bag
- $KSD_{norm}$ represents an individual mean diameter of the capsular bag
- $KHD_{norm}$ represents an empirically determined diameter of the capsulorhexis as a function of various parameters
- wherein at least one of pathology, ethnic origin, sex, and age are taken into account as empirical scaling functions.

9. The method according to claim 5, wherein $f(V1_{KSD-KHD})$ results as a function from the ratio of the capsular bag to capsulorhexis diameters from formula (4):

$$f(V1_{KSD-KHD})=KHD/KSD \cdot KSD_{norm}/KHD_{norm} \quad (4)$$

in which
- KHD represents the diameter of the capsulorhexis
- KSD represents the diameter of the capsular bag
- $KSD_{norm}$ represents an individual mean diameter of the capsular bag
- $KHD_{norm}$ represents an empirically determined diameter of the capsulorhexis as a function of various parameters
- wherein at least one of pathology, ethnic origin, sex, and age are taken into account as empirical scaling functions.

10. The method according to at least one of the claim 5, wherein $f(V2_{KSP-LHD})$ results as a function from the ratio of the diameter of the capsular bag to the lens the lens haptic from formula (5):

$$f(V2_{KSD-LHD})=LHD/KSD \cdot KSD_{norm}/LHD \quad (5)$$

in which
- LHD characterizes the specific diameter of the lens haptic
- KSD characterizes the diameter of the capsular bag and
- $KSD_{norm}$ characterizes an individual mean diameter of the capsular bag
- wherein at least one of pathology, ethnic origin, sex, and age are taken into account as empirical scaling functions.

11. The method according to claim 1, further comprising describing the anatomical, postoperative lens orientation ($LL_{an-post}$) by the following three parameters:
- LDZ—horizontal and vertical decentration of the lens,
- LVK—horizontal and vertical tilting of the lens, and
- PBM—center of the pupil region that can be used in the calculation.

12. The method according to claim 2, further comprising describing the anatomical, postoperative lens orientation ($LL_{an-post}$) by the following three parameters:
- LDZ—horizontal and vertical decentration of the lens,
- LVK—horizontal and vertical tilting of the lens, and
- PBM—center of the pupil region that can be used in the calculation.

13. The method according to claim 1, further comprising determining the horizontal and vertical decentration LDZ of the lens results from formula (6):

$$LDZ=LDZ_{eye} \cdot f(LDZ_{eye}) \quad (6)$$

in which
- $LDZ_{eye}$ represents the horizontal and vertical decentration of the actual eye lens and
- $f(LDZ_{eye})$ represents an empirical function of the decentration of the actual eye lens
- wherein at least one of pathology, ethnic origin, sex, and age are taken into account as empirical scaling functions.

14. The method according to claim 2, further comprising determining the horizontal and vertical decentration LDZ of the lens results from formula (6):

$$LDZ=LDZ_{eye} \cdot f(LDZ_{eye}) \quad (6)$$

in which
- $LDZ_{eye}$ represents the horizontal and vertical decentration of the actual eye lens and
- $f(LDZ_{eye})$ represents an empirical function of the decentration of the actual eye lens
- wherein at least one of pathology, ethnic origin, sex, and age are taken into account as empirical scaling functions.

15. The method according to claim 11, further comprising determining the horizontal and vertical decentration LDZ of the lens results from formula (6):

$$LDZ=LDZ_{eye} \cdot f(LDZ_{eye}) \quad (6)$$

in which
- $LDZ_{eye}$ represents the horizontal and vertical decentration of the actual eye lens and
- $f(LDZ_{eye})$ represents an empirical function of the decentration of the actual eye lens
- wherein at least one of pathology, ethnic origin, sex, and age are taken into account as empirical scaling functions.

16. The method according to claim 1, further comprising determining the horizontal and vertical tilting LVK of the lens results from formula (7):

$$LVK=LVK_{eye} \cdot f(LVK_{eye}) \quad (7)$$

whereby $LVK_{eye}$ represents the horizontal and vertical tilting of the actual eye lens and $f(LVK_{eye})$ represents an empirical function of the tilting of the decentration of the actual eye lens
wherein at least one of pathology, ethnic origin, sex, and age are taken into account as empirical scaling functions.

17. The method according to claim 2, further comprising determining the horizontal and vertical tilting LVK of the lens results from formula (7):

$$LVK = LVK_{eye} \times f(LVK_{eye}) \quad (7)$$

whereby $LVK_{eye}$ represents the horizontal and vertical tilting of the actual eye lens and $f(LVK_{eye})$ represents an empirical function of the tilting of the decentration of the actual eye lens wherein at least one of pathology, ethnic origin, sex, and age are taken into account as empirical scaling functions.

18. The method according to claim 11, further comprising determining the horizontal and vertical tilting LVK of the lens results from formula (7):

$$LVK = LVK_{eye} \times f(LVK_{eye}) \quad (7)$$

whereby $LVK_{eye}$ represents the horizontal and vertical tilting of the actual eye lens and $f(LVK_{eye})$ represents an empirical function of the tilting of the decentration of the actual eye lens wherein at least one of pathology, ethnic origin, sex, and age are taken into account as empirical scaling functions.

19. The method according to claim 1, further comprising determining the center of the pupil region PBM that is used for the calculation from formula (8):

$$PBM = HHV - PDZ - LDZ \quad (8)$$

in which HHV represents the corneal vertex,
PDZ represents the horizontal and vertical decentration of the pupil and
LDZ represents the horizontal and vertical decentration of the lens.

20. The method according to claim 2, further comprising determining the center of the pupil region PBM that is used for the calculation from formula (8):

$$PBM = HHV - PDZ - LDZ \quad (8)$$

in which HHV represents the corneal vertex,
PDZ represents the horizontal and vertical decentration of the pupil and
LDZ represents the horizontal and vertical decentration of the lens.

21. The method according to claim 11, further comprising determining the center of the pupil region PBM that is used for the calculation from formula (8):

$$PBM = HHV - PDZ - LDZ \quad (8)$$

in which HHV represents the corneal vertex,
PDZ represents the horizontal and vertical decentration of the pupil and
LDZ represents the horizontal and vertical decentration of the lens.

22. The method according to claim 11, wherein the center of the pupil region PBM that can be used for the calculation can refer to various pupil apertures, including for photopic, scotopic, or mesopic vision.

23. The method according to claim 13, wherein the center of the pupil region PBM that can be used for the calculation can refer to various pupil apertures, including for photopic, scotopic, or mesopic vision.

24. The method according to claim 1, further comprising using geometric-optical formulas or ray tracing to calculate the intraocular lens (L) to be implanted in the pseudophakic eye.

* * * * *

UNITED STATES PATENT AND TRADEMARK OFFICE
CERTIFICATE OF CORRECTION

PATENT NO. : 9,545,341 B2  
APPLICATION NO. : 14/130120  
DATED : January 17, 2017  
INVENTOR(S) : Wilfried Bissmann et al.

Page 1 of 1

It is certified that error appears in the above-identified patent and that said Letters Patent is hereby corrected as shown below:

In the Specification

Column 4, Line 63, after "type", insert --.--

Column 5, Line 8 (equation 4), delete the existing equation and insert the following equation
--$f(V^1_{KSD-DHD})=KHD/KSD \cdot KSD_{norm}/KHD_{norm}$--

Column 6, Line 11, delete existing equation 6 and insert the following equation
--$LDZ=LDZ_{eye}{}^x f(LDZ_{eye})$--

Column 6, Line 23, delete existing equation 7 and insert the following equation
--$LVK=LVK_{eye}{}^x f(LVK_{eye})$--

Column 6, Line 61, after "fit-ability", insert --fit-ability"--

Column 7, Line 39, delete "take", insert --taken--

Column 8, Line 8, delete "$V1_{KSD-KHD}$", insert --$V1_{KSD-LHD}$--

In the Claims

Column 8, Line 60, Claim 3 delete "$f(V2_{KSD-KHD})$", insert --$f(V2_{KSD-LHD})$--

Column 8, Line 60, Claim 3 delete "ration", insert --ratio--

Column 8, Line 61, Claim 3 delete "diameter s", insert --diameters--

Column 9, Line 54, Claim 10 delete "$f(V2_{KSP-LHD})$", insert --$f(V2_{KSD-LHD})$--

Column 9, Line 55, Claim 10 delete the first occurrence or "the lens"

Signed and Sealed this  
Twenty-sixth Day of December, 2017

Joseph Matal  
*Performing the Functions and Duties of the*  
*Under Secretary of Commerce for Intellectual Property and*  
*Director of the United States Patent and Trademark Office*